US007932352B2

(12) United States Patent
Inagaki et al.

(10) Patent No.: US 7,932,352 B2
(45) Date of Patent: Apr. 26, 2011

(54) SEMAPHORIN GENES (I)

(75) Inventors: Shinobu Inagaki, Ibaraki (JP); Tatsuo Furuyama, Ibaraki (JP)

(73) Assignee: Dainippon Sumitomo Pharma Co., Ltd., Osaka-Shi, Osaka (JP)

( * ) Notice: Subject to any disclaimer, the term of this patent is extended or adjusted under 35 U.S.C. 154(b) by 146 days.

(21) Appl. No.: 12/325,089

(22) Filed: Nov. 28, 2008

(65) Prior Publication Data

US 2009/0088557 A1 Apr. 2, 2009

Related U.S. Application Data

(62) Division of application No. 10/144,031, filed on May 14, 2002, now abandoned, which is a division of application No. 09/308,179, filed as application No. PCT/JP97/04111 on Dec. 11, 1997, now Pat. No. 6,436,669.

(30) Foreign Application Priority Data

Nov. 15, 1996 (JP) ...................................... 8-321068

(51) Int. Cl.
C07K 14/435 (2006.01)
(52) U.S. Cl. ......................... 530/350; 530/395; 530/399
(58) Field of Classification Search .................. None
See application file for complete search history.

(56) References Cited

U.S. PATENT DOCUMENTS

| 5,416,197 A | 5/1995 | Raper et al. |
| 5,616,491 A | 4/1997 | Mak et al. |
| 5,639,856 A | 6/1997 | Goodman et al. |
| 5,684,133 A | 11/1997 | Schwab et al. |
| 5,807,826 A | 9/1998 | Goodman et al. |
| 5,807,862 A | 9/1998 | Klein et al. |
| 5,935,865 A | 8/1999 | Goodman et al. |

FOREIGN PATENT DOCUMENTS

| EP | 0396719 | 11/1990 |
| WO | WO-94/17831 | 8/1994 |
| WO | WO-95/07706 | 3/1995 |
| WO | WO-97/20928 | 6/1997 |

OTHER PUBLICATIONS

C. C. Cristensen et al., Genbank, Definition: "M. musculus mRNA for semaphorin H", Locus: MMSEMH Accession Z80941 (Oct. 11, 1996).
M.D. Adams et al., Genbank, Definition: EST86074 Homo Sapiens cDNA 5' end similar to semaphorin III Locus: T29595 Accession T29595 (Sep. 6, 1995).
T. Nagase et al., GenBank, Definition: "Human mRNA for KIAA0331 gene, complete cds.", Locus: AB002329, Accession: AB002329 (Mar. 28, 1997).
L. Hillier et al., GenBank, "The WashU-Merck EST Project" (1995).
M. Marra et al., GenBank, "The WashU-HHMT Mouse EST Project". Locus: AA107420, Accession: AA107420 (1996).
Kolodkin et al., Cell, vol. 75, 1389-1399 (Dec. 1993).
Schwab et al., The Journal of Neuroscience, vol. 8(7), 2381-2393 (Jul. 1988).
Bandtlow et al., Science, vol. 259, 80-83 (Jan. 1993).
Alan R. Johnson, Bioessays, vol. 15, No. 12, 807-813 (Dec. 1993).
Clifford J. Woolf, Nature, vol. 378, 339-440 (Nov. 1995).
Kikucho et al., Molecular Brain Research 51, 229-237 (1997).
Schnell et al., Nature, vol. 343, 269-272 (Jan. 1990).
Luo et al., Cell, vol. 75, 217-227 (Oct. 1993).
Bregman et al., Nature, vol. 378, 498-501 (Nov. 1995).
Dodd et al., Cell, vol. 81, 471-474 (May 1995).
Kolodkin et al., Neuron, vol. 9, 831-845 (Nov. 1992).
Puschel et al., Neuron, vol. 14, 941-948 (May 1995).
Zhou et al., Molecular and Cellular Neuroscience 9, 26-41 (1997).
Matthes et al., Cell, vol. 81, 631-639 (May 1995).
Messersmith et al., Neuron, vol. 14, 949-959 (May 1995).
Schwab et al., Annu. Rev. Neurosci. 16, 565-595 (1993).
Richardson et al., Nature, vol. 284, 264-265 (Mar. 1980).
David et al., Science, vol. 214, 931-933 (Nov. 1981).
Luo et al., Neuron, vol. 14, 1131-1140 (Jun. 1995).
Eckhardt et al., Molecular and Cellular Neuroscience 9, 409-419 (1997).
Koppel et al., Neuron, vol. 19, 531-537 (Sep. 1997).
Furuyama et al., The Journal of Biological Chemistry, vol. 271, No. 52, 33376-33381 (1996).
Mangasser-Stephan et al., Biochemical and Biophysical Research Communications 234, 153-156 (1997).
Herold et al., The Journal of Immunology, 5262-5268 (1996).
Pursel et al., J. Reprod. Fert. Suppl., vol. 40, pp. 235-245 (1990).
Louis-Marie Houdebine, Journal of Biotechnology, vol. 34, pp. 269-287 (1994).
Wu et al., "New Strategies for Gene Knockout" in Methods in Gene Technology, CRC press, Inc. Boca Raton, Florida, USA, pp. 339-365 (May 1997).
Luo et al., Pir60 Accession No. A49069 (Apr. 1994).
Luo et al., Cell, vol. 75, pp. 217-227 (Oct. 1993).
Bentley et al., Geneseq Accession No. Q87442 (Mar. 1995).
Palmiter et al., Science, vol. 222, pp. 809-814 (Nov. 1983).
J. Rudinger, Peptide Hormones, Parsons, University Park Press, Baltimore, pp. 1-7 (Jun. 1976).
Goshima et al., "Collapsin-induced growth cone collapse mediated by an intracellular protein related to UNC-33", Nature, vol. 376, 509-514 (Aug. 1995).

*Primary Examiner* — Jeffrey Stucker
*Assistant Examiner* — Stephen Gucker
(74) *Attorney, Agent, or Firm* — Birch, Stewart, Kolasch & Birch, LLP

(57) ABSTRACT

The present invention provides a novel Semaphorin having neurite-outgrowth inhibition activity or proteins analogous thereto, peptide fragments of, or antibodies against, such proteins, genes encoding such proteins, expression vectors for said genes, transformed cells into which said expression vectors have been introduced, methods for producing a recombinant protein which employ said transformed cells, antisense nucleotides against the above genes, transgenic animals involving insertion or deletion of the above genes, and screening methods for antagonists of the above proteins, all of which are useful mainly in diagnoses, treatments, or studies relating to neurological diseases. The present invention further provides use of such proteins, peptides, antibodies, genes, or antisense nucleotides as pharmaceutical or diagnostic agents or laboratory reagents.

4 Claims, 2 Drawing Sheets

SEQUENCE LISTING

<160> NUMBER OF SEQ ID NOS: 4

<210> SEQ ID NO 1
<211> LENGTH: 775
<212> TYPE: PRT
<213> ORGANISM: Mus sp.

<400> SEQUENCE: 1

```
Met Ala Pro Ala Gly His Ile Leu Thr Leu Leu Leu Trp Gly His Leu
1               5                   10                  15

Leu Glu Leu Trp Thr Pro Gly His Ser Ala Asn Pro Ser Tyr Pro Arg
            20                  25                  30

Leu Arg Leu Ser His Lys Glu Leu Leu Glu Leu Asn Arg Thr Ser Ile
        35                  40                  45

Phe Gln Ser Pro Leu Gly Phe Leu Asp Leu His Thr Met Leu Leu Asp
    50                  55                  60

Glu Tyr Gln Glu Arg Leu Phe Val Gly Gly Arg Asp Leu Val Tyr Ser
65                  70                  75                  80

Leu Asn Leu Glu Arg Val Ser Asp Gly Tyr Arg Glu Ile Tyr Trp Pro
                85                  90                  95

Ser Thr Ala Val Lys Val Glu Glu Cys Ile Met Lys Gly Lys Asp Ala
            100                 105                 110

Asn Glu Cys Ala Asn Tyr Ile Arg Val Leu His His Tyr Asn Arg Thr
        115                 120                 125

His Leu Leu Thr Cys Ala Thr Gly Ala Phe Asp Pro His Cys Ala Phe
```

-continued

```
            130                 135                 140
Ile Arg Val Gly His His Ser Glu Glu Pro Leu Phe His Leu Glu Ser
145                 150                 155                 160

His Arg Ser Glu Arg Gly Arg Gly Arg Cys Pro Phe Asp Pro Asn Ser
                165                 170                 175

Ser Phe Val Ser Thr Leu Val Gly Asn Glu Leu Phe Ala Gly Leu Tyr
                180                 185                 190

Ser Asp Tyr Trp Gly Arg Asp Ser Ala Ile Phe Arg Ser Met Gly Lys
                195                 200                 205

Leu Gly His Ile Arg Thr Glu His Asp Asp Glu Arg Leu Leu Lys Glu
210                 215                 220

Pro Lys Phe Val Gly Ser Tyr Met Ile Pro Asp Asn Glu Asp Arg Asp
225                 230                 235                 240

Asp Asn Lys Met Tyr Phe Phe Thr Glu Lys Ala Leu Glu Ala Glu
                245                 250                 255

Asn Asn Ala His Thr Ile Tyr Thr Arg Val Gly Arg Leu Cys Val Asn
                260                 265                 270

Asp Met Gly Gly Gln Arg Ile Leu Val Asn Lys Trp Ser Thr Phe Leu
            275                 280                 285

Lys Ala Arg Leu Val Cys Ser Val Pro Gly Met Asn Gly Ile Asp Thr
290                 295                 300

Tyr Phe Asp Glu Leu Glu Asp Val Phe Leu Leu Pro Thr Arg Asp Pro
305                 310                 315                 320

Lys Asn Pro Val Ile Phe Gly Leu Phe Asn Thr Thr Ser Asn Ile Phe
                325                 330                 335

Arg Gly His Ala Val Cys Val Tyr His Met Ser Ser Ile Arg Glu Ala
                340                 345                 350

Phe Asn Gly Pro Tyr Ala His Lys Glu Gly Pro Glu Tyr His Trp Ser
            355                 360                 365

Leu Tyr Glu Gly Lys Val Pro Tyr Pro Arg Pro Gly Ser Cys Ala Ser
            370                 375                 380

Lys Val Asn Gly Gly Lys Tyr Gly Thr Thr Lys Asp Tyr Pro Asp Asp
385                 390                 395                 400

Ala Ile Arg Phe Ala Arg Met His Pro Leu Met Tyr Gln Pro Ile Lys
                405                 410                 415

Pro Val His Lys Lys Pro Ile Leu Val Lys Thr Asp Gly Lys Tyr Asn
                420                 425                 430

Leu Arg Gln Leu Ala Val Asp Arg Val Glu Ala Glu Asp Gly Gln Tyr
            435                 440                 445

Asp Val Leu Phe Ile Gly Thr Asp Thr Gly Ile Val Leu Lys Val Ile
450                 455                 460

Thr Ile Tyr Asn Gln Glu Thr Glu Trp Met Glu Glu Val Ile Leu Glu
465                 470                 475                 480

Glu Leu Gln Ile Phe Lys Asp Pro Ala Pro Ile Ile Ser Met Glu Ile
                485                 490                 495

Ser Ser Lys Arg Gln Gln Leu Tyr Ile Gly Ser Ala Ser Ala Val Ala
                500                 505                 510

Gln Val Arg Phe His His Cys Asp Met Tyr Gly Ser Ala Cys Ala Asp
                515                 520                 525

Cys Cys Leu Ala Arg Asp Pro Tyr Cys Ala Trp Asp Gly Ile Ser Cys
            530                 535                 540

Ser Arg Tyr Tyr Pro Thr Gly Ala His Ala Lys Arg Arg Phe Arg Arg
545                 550                 555                 560
```

```
Gln Asp Val Arg His Gly Asn Ala Ala Gln Gln Cys Phe Gly Gln Gln
            565                 570                 575

Phe Val Gly Asp Ala Leu Asp Arg Thr Glu Glu Arg Leu Ala Tyr Gly
        580                 585                 590

Ile Glu Ser Asn Ser Thr Leu Leu Glu Cys Thr Pro Arg Ser Leu Gln
    595                 600                 605

Ala Lys Val Ile Trp Phe Val Gln Lys Gly Arg Asp Val Arg Lys Glu
610                 615                 620

Glu Val Lys Thr Asp Asp Arg Val Val Lys Met Asp Leu Gly Leu Leu
625                 630                 635                 640

Phe Leu Arg Val Arg Lys Ser Asp Ala Gly Thr Tyr Phe Cys Gln Thr
                645                 650                 655

Val Glu His Asn Phe Val His Thr Val Arg Lys Ile Thr Leu Glu Val
            660                 665                 670

Val Glu Glu His Lys Val Glu Gly Met Phe His Lys Asp His Glu Glu
        675                 680                 685

Glu Arg His His Lys Met Pro Cys Pro Leu Ser Gly Met Ser Gln
    690                 695                 700

Gly Thr Lys Pro Trp Tyr Lys Glu Phe Leu Gln Leu Ile Gly Tyr Ser
705                 710                 715                 720

Asn Phe Gln Arg Val Glu Glu Tyr Cys Glu Lys Val Trp Cys Thr Asp
                725                 730                 735

Lys Lys Arg Lys Lys Leu Lys Met Ser Pro Ser Lys Trp Lys Tyr Ala
            740                 745                 750

Asn Pro Gln Glu Lys Arg Leu Arg Ser Lys Ala Glu His Phe Arg Leu
        755                 760                 765

Pro Arg His Thr Leu Leu Ser
    770                 775

<210> SEQ ID NO 2
<211> LENGTH: 2898
<212> TYPE: DNA
<213> ORGANISM: Mus sp.
<220> FEATURE:
<221> NAME/KEY: misc_feature
<222> LOCATION: (1)..(2898)
<223> OTHER INFORMATION: Strandedness: Double-stranded
<220> FEATURE:
<221> NAME/KEY: misc_feature
<222> LOCATION: (1)..(2898)
<223> OTHER INFORMATION: any n = a, c, g, t, unknown, or other

<400> SEQUENCE: 2
ctgcaggatg gccctgtcct gttcggtgac tcggctctgc ttcttgcggc cgaacaggtt      60
gcccatggcg ccccgcgcc ggctcgtgcc gaattcggca cgagccagcc cggacctggc     120
tctcaagacg cgctccttgg acggtctctt gctccgcgct ctaaccacc gggcccaagg     180 acagaaaggc ttagcggatc caaatattgc ccggcaaatg cacttgggaa atggtatttt     240
ctgatgacaa ccccttctgt tgtgacaaa gcctgtcgcc cgcagttgcc cctggaggga     300
agtactaagt aaaactcaat cctgtcttaa agtgtggctg caggggccag aggagagcca     360
gcacgcacca tggcaccggc cggacacatc ctcaccttgc tgctctgggg tcacctgctg     420
gaactctgga ccccaggtca ctccgcgaac ccctcctacc ccaggctacg cctgtcacat     480
aaagaacttt tggaactgaa taggacttca atatttcaaa gccccttgg atttcttgat     540 ctccatacaa tgctgctgga tgagtatcaa gaacggctct tgtgggagg cagagacctt     600 gtctattccc tgaacttgga acgagtcagt gacggctaca gagagatata ctggccgagc     660
```

```
acagcagtaa aggtagaaga atgcataatg aaaggaaaag acgcaaatga gtgtgccaat    720
tatatccggg ttttgcatca ctacaacagg acacaccttc tgacctgtgc tactggagct    780
tttgatccac actgtgcctt catcagagtc gggcaccatt cagaggaacc cctgtttcac    840
ctggagtcac acagatctga gagaggaagg ggcagatgtc cttttgaccc caactcctcc    900
tttgtgtcca cgctagttgg gaatgagctg tttgctggac tctacagtga ctattggggc    960
agagactcgg cgatcttccg cagcatgggg aagttaggcc atattcgcac tgagcatgac   1020
gatgagcggc tcctgaaaga accaaaattt gtaggttcat atatgattcc tgataacgaa   1080
gaccgagatg acaacaaaat gtacttttc tttactgaga aggcgctgga ggcggagaac    1140
aacgcccaca cgatctacac ccgagtgggg cggctgtgcg tgaatgacat gggaggacag   1200
agaatcctgg tgaacaagtg gagcactttc cttaaagcgc ggctggtttg ctcagtgccg   1260
ggaatgaatg gaatcgacac atactttgac gaactagagg atgtgttttt actgccgacc   1320
agagatccta agaatccagt gatatttgga ctgtttaata ctaccagcaa tatatttaga   1380
ggccatgctg tatgtgtgta tcacatgtca agtatccggg aagcctttaa tggcccatat   1440
gctcataaag aaggccctga ataccactgg tcactatatg aaggaaaagt cccctaccca   1500
aggcctggtt cctgtgccag caaagtaaac ggaggcaagt atggaaccac caaagattac   1560
cccgatgacg ccatccggtt cgcaaggatg catcctctaa tgtatcagcc cataaaacct   1620
gttcataaaa aaccaatact ggtaaaaaca gatggaaaat acaacctgag gcaacttgcc   1680
gtggatcggg tggaagcgga ggatggccag tatgacgtct tatttattgg gacagacaca   1740
ggaattgtgc tgaaagtaat cacaatttac aaccaagaaa cagagtggat ggaggaagtc   1800
attctagagg aacttcaaat attcaaggat ccagcccccta tcatttctat ggaaatttct   1860
tcaaagagac aacagcttta cattggatca gcctctgctg tggcacaagt cagattccat   1920
cactgcgaca tgtatggcag tgcttgtgct gactgctgcc tggctcgaga cccgtactgt   1980
gcctgggatg gcatatcctg ctccaggtac tacccaacag gtgcacacgc aaagaggagg   2040
ttccgcaggc aggacgttcg gcatggcaac gccgcccaac agtgctttgg acagcaattt   2100
gttggagacg cgttggacag gactgaagag aggctggctt atggcataga gagcaacagt   2160
actctgttgg aatgcacccc gcgatcacta caagcaaaag tcatctggtt tgtacagaag   2220
ggacgcgacg taagaaaaga agaggtgaag acgatgaca gagttgtcaa gatggacttg   2280
ggcttgctct tcctcagagt acgcaagtca gatgcaggga cctattttg ccagacagta    2340
gaacacaatt ttgtccatac tgtgcgtaaa atcaccttgg aggtggtcga agagcataaa   2400
gtggagggca tgtttcataa ggaccatgaa gaggaaagac atcacaagat gccctgccct   2460
cccttaagcg gtatgtctca ggggacaaaa ccgtggtaca aggaattctt gcagctgatt   2520
ggctacagca acttccagag agtggaagaa tactgcgaaa aggtgtggtg tacagataag   2580
aagaggaaaa agcttaaaat gtctccctcc aagtggaagt atgccaaccc caggaaaag    2640
aggcttcgct ctaaagctga gcacttccgc ctgcccaggc acacgctgct ctcctgaggg   2700
cgccctctgc cggcggctga ggaacctagg atggaaacat tttttaaag ggggggaaaa    2760
aaaaaagact gaaagcatgc agtctctttc cattacttca agaactttc tgtagtactn   2820
agaggctggg aaggtgtttt aagttattct gcatattcat ctgactgtac aaacatctct   2880
ctcacagtac ttggtact                                                 2898

<210> SEQ ID NO 3
<211> LENGTH: 20
<212> TYPE: DNA
```

-continued

```
<213> ORGANISM: Artificial Sequence
<220> FEATURE:
<223> OTHER INFORMATION: Description of Artificial Sequence: synthetic
      oligonucleotide primer
<220> FEATURE:
<221> NAME/KEY: misc_feature
<222> LOCATION: (1)..(20)
<223> OTHER INFORMATION: any n = a, c, g, t, unknown, or other

<400> SEQUENCE: 3
tacgacgtnh tnttyathgg                                                      20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide primer
<220> FEATURE:
<221> NAME/KEY: modified_base
<222> LOCATION: (6)..(15)
<223> OTHER INFORMATION: any n =  i

<400> SEQUENCE: 4
tcccangcrc artanggrtc                                                      20
```

SEMAPHORIN GENES (I)

This application is a Divisional of application Ser. No. 10/144,031 filed on May 14, 2002, now abandoned, and for which priority is claimed under 35 U.S.C. §120; and which is a Divisional of U.S. application Ser. No. 09/308,179 filed on May 14, 1999; now U.S. Pat. No. 6,436,669, which is the International Phase Application of International Application No. PCT/JP97/04111 filed on Dec. 11, 1997; and this application claims priority of Application No. 8/321068 filed in Japan on Nov. 15, 1996 under 35 U.S.C. §119; the entire contents of all are hereby incorporated by reference.

TECHNICAL FIELD

The present invention relates to a novel Semaphorin belonging to the Semaphorin family and a gene therefor. More particularly, it relates to a novel Semaphorin having neurite outgrowth inhibition activity and proteins analogous thereto, or peptide fragments of, or antibodies against, such proteins, genes (DNAs) encoding such proteins, expression vectors for said genes, transformed cells into which said expression vectors have been introduced, methods for producing a recombinant protein which employ said transformed cells, antisense nucleotides against the above genes, transgenic animals involving insertion or deletion of the above genes, or screening methods for antagonists of the above proteins, and it further relates to use of such proteins, peptides, antibodies, genes, antisense nucleotides or the like as pharmaceutical or diagnostic agents or laboratory reagents.

BACKGROUND ART

In 1992, Fasciclin IV (latterly called G-Sema I) was cloned as one of the genes involved in guidance for neuron in grasshopper. The next year, the existence of a gene family of which members encode analogous domains and are distributed in a wide range of species covering insects, viruses, nematodes, and human was revealed, and the gene family members were designated "Semaphorin genes". To date, more than ten genes belonging to the Semaphorin family have been reported (*Cell*, 81, 471-474 (1995)).

These Semaphorin genes characteristically contains, in the amino acid sequences which they encode, similar structures called semaphorin domain each consisting of about 500 amino acids (*Neuron*, 14, 941-948 (1995); *Cell*, 7, 1389-1399 (1993)). Although the homologies of the above amino acid sequences among Semaphorins are 80-20% and are thus not always high, some of the amino acid residues are extremely well conserved as exemplified by thirteen cysteine residues located at conserved positions. In the regions other than semaphorin domains, Semaphorins are highly varied one another. Specifically, Semaphorins include both of secretory and membrane-bound forms, and have various structures including those having Ig domains, thrombospondin domains, or a cluster of basic amino acids at its carboxy terminus.

Among such Semaphorins, functions have been verified for only a few, including, for example, Fasciclin IV of grasshopper, Semaphorins I and II of *drosophila*, Collapsin of chick, and Semaphorin III which corresponds to Collapsin in mammals. All of these Semaphorins are, however, known to inhibit axon outgrowth and synapsis formation during the stage of ontogenesis, that is, in the course of the neural network formation at the embryonic or fetal stage (*Neuron*, 14, 941-948 (1995); *Neuron*, 14, 949-959 (1995); *Cell*, 8, 631-639 (1995); *Cell*, 75, 1389-1399 (1993); *Cell*, 75, 217-227 (1993); and *Neuron*, 9, 831-845 (1992)).

Although Semaphorin genes are known to perform its function at the ontogenetic stage as described above, it has not yet been ascertained whether or not they perform any function also in the adult. However, some Semaphorin genes are known to be expressed also in the adult in which formation of the neural network has been already completed, suggesting that they may have some function also in said adult. For example, the central nervous system (CNS) in the adult is widely known to lack regenerating ability, and some Semaphorins which inhibit neurite outgrowth may conceivably function as a CNS-neuron regeneration inhibitor in the adult (*Nature*, 378, 439-440 (1995)). In addition, it has been suggested, by a recently reported study on Semaphorin III-knockout mouse, that a certain Semaphorin may probably act in inhibiting the growth of cardiac muscles (*Nature*, 383, 525-528 (1996)). Furthermore, a certain Semaphorin has been suggested to be involved in survival and aggregation of B lymphocytes (*Proc. Natl. Acad. Sci. USA*, 93, 11780-11785 (1996))

It is thus being demonstrated that Semaphorins play important roles not only in the nervous system but also in non-nervous systems, and therefor attracting great interest in studies on said Semaphorins.

PROBLEM TO BE SOLVED BY THE INVENTION

Accordingly, an object of the present invention is to provide a novel Semaphorin and proteins analogous thereto, peptide fragments of, or antibodies against, such proteins, genes (DNAs) encoding such proteins, expression vectors for said genes, transformed cells into which said expression vectors have been introduced, methods for producing a recombinant protein which employ said transformed cells, antisense nucleotides against the above genes, transgenic animals involving insertion or deletion of the above genes, or screening methods for antagonists of the above proteins, all of which are useful for medical treatments, diagnoses, or studies of neurological diseases, and to further provide use of such proteins, peptides, antibodies, genes, antisense nucleotide or the like as pharmaceutical or diagnostic agents or laboratory reagents.

MEANS OF SOLVING THE PROBLEM

Despite the increasing interest in studies on Semaphorin as described above, not all structures of the presumably more than twenty kinds of Semaphorin genes have been elucidated. The present inventors have planed to clone unknown Semaphorins by making use of gene regions homologous among known Semaphorins. Firstly, we aimed at a region homologous between Collapsin derived from chick and G-Sema I derived from grasshopper, and used it to prepare synthetic primers for amplifying a fragment corresponding to this region. Although it was uncertain whether or not the use of these synthetic primers may result in successful cloning of any novel Semaphorin other than Collapsin and G-Sema I, we performed PCR using the synthetic primers with cDNAs derived from mouse embryo as a template. As a result, we have succeeded in cloning a novel Semaphorin gene.

Analysis revealed that the novel Semaphorin of the present invention contains no transmembrane regions in its structure, indicating that it belongs to the secretory Semaphorin subfamily. Although five to six Semaphorins of the secretory type have been hitherto known, only one of such Semaphorins has demonstrated activities. The Semaphorin of the present invention is of the secretory type, and therefore, is characterized in that it may serve, as such, as a pharmaceutical or diagnostic agent or laboratory reagent in the art.

It was also shown, by further investigations on the Semaphorin of the present invention, that it inhibits neurite outgrowth, and that expression of the gene begins at the embryonal stage, and in the adult, the gene is characteristically expressed in a wide range of central and peripheral tissues in a localized manner.

Thus, the gist of the present invention relates to:
(1) a gene encoding the following protein (a) or (b):
(a) a protein comprising the amino acid sequence shown in SEQ ID NO: 1,
(b) a protein which comprises an amino acid sequence wherein one or more amino acids are deleted, substituted and/or added in the amino acid sequence shown in SEQ ID NO: 1, and which protein has neurite-outgrowth inhibition activity;
(2) a gene comprising the following DNA (a) or (b):
(a) DNA comprising the base sequence shown in SEQ ID NO: 2,
(b) DNA which hybridizes under stringent conditions to DNA comprising the base sequence shown in SEQ ID NO: 2, and which encodes a protein having neurite-outgrowth inhibition activity;
(3) DNA which is cloned from a human cDNA library or a human genomic library, and which hybridizes under stringent conditions to DNA comprising at least part of DNA consisting of the base sequence shown in SEQ ID NO: 2;
(4) a protein obtained by expressing either a gene of the above item (1) or (2), or DNA of the above item (3);
(5) an expression vector which contains either a gene of the above item (1) or (2), or DNA of the above item (3);
(6) a transformant obtained by introduction of an expression vector of the above item (5);
(7) a transformant of the above item (6) in which a gene of the above item (1) or (2), or DNA of the above item (3), existing in an expression vector of the above item (5) is stably retained;
(8) a process for producing a recombinant protein, which process comprises culturing a transformant of the above item (6) or (7), and recovering the recombinant protein expressed;
(9) a peptide comprising a segment of at least six or more amino acids of a protein of the above item (4);
(10) an antisense nucleotide, or chemically modified variant thereof, which is directed against a segment of at least eight or more bases of a gene of the above item (1) or (2), or of DNA of the above item (3);
(11) an antisense nucleotide, or chemically modified variant thereof, of the above item (10), which inhibits expression of a protein of the above item (4) when introduced into cells;
(12) an antibody or its fragment which specifically binds to a protein of the above item (4) or to a peptide of the above item (9);
(13) a pharmaceutical agent comprising, as an active ingredient, a gene of the above item (1) or (2), DNA of the above item (3), a protein of the above item (4), a peptide of the above item (9), an antisense nucleotide or chemically modified variant thereof of the above item (10) or (11), or an antibody or its fragment of the above item (12);
(14) a neurite outgrowth inhibitor for PNS-neurons, characterized in that it contains at least one of the proteins of the above item (4);
(15) a screening method for antagonists of a protein comprising the amino acid sequence shown in SEQ ID NO: 1, characterized in that it employs a protein of the above item (4); and
(16) a transgenic animal in which either a gene of the above item (1) or (2), or DNA of the above item (3) has been artificially inserted into its chromosome, or has been knocked out.

MODE FOR CARRYING OUT THE INVENTION

For the purpose of the present invention, "gene" is also referred to as "DNA". The gene is not specifically restricted so far as it encodes a protein having the neurite-outgrowth inhibition activity according to the novel Semaphorin. Examples are novel mouse Semaphorin genes such as a gene encoding a protein which comprises the amino acid sequence shown in SEQ ID NO: 1 of the sequence listing or a gene comprising the base sequence shown in SEQ ID NO: 2 of the sequence listing. Also included in the genes of the present invention are those genes encoding a protein which comprises an amino acid sequence wherein one or more amino acids are deleted, substituted and/or added in the amino acid sequence shown in SEQ ID NO: 1, and those genes which hybridize under stringent conditions to DNA comprising the base sequence shown in SEQ ID NO: 2, provided that they encode proteins having neurite-outgrowth inhibition activity. These genes are explained below in order.

1) Gene Encoding a Novel Mouse Semaphorin

Of the above-mentioned genes, "a gene which encodes a protein comprising the amino acid sequence shown in SEQ ID NO: 1" or "a gene comprising the base sequence shown in SEQ ID NO: 2" is a novel mouse Semaphorin gene cloned in the present invention.

Such genes may be cloned, for example, as follows: PCR may be performed using single-stranded cDNAs derived from mouse embryo as a template with oligonucleotide primers which can amplify the region homologous between two known Semaphorins, in this case Collapsin and G-Sema I, and the resulting amplified fragment may be used as a probe for screening cDNA libraries such as those derived from adult mouse brain to clone the desired gene. Particular techniques for such cloning may be found in the standard texts such as "Molecular Cloning", 2nd ed., Cold Spring Harbor Laboratory Press (1989). PCR may be performed, for example, by making reference to "PCR", IRL Press (1991). The base sequence of cloned DNA may be determined by conventional methods, for example, using a sequencing kit commercially available.

When compared with previously reported Semaphorin genes, the novel Semaphorin gene of the present invention exhibits 54% overall identity with mouse Semaphorin D (a mouse homolog of chick Collapsin) at the amino acid level, and exhibits 85% identity with chick Collapsin-5, of which sequence is known only partially, in their semaphorin domains.

2) Gene Encoding Modified Protein of the Novel Semaphorin

Of the above-mentioned genes, "a gene encoding a protein which comprises an amino acid sequence wherein one or more amino acids are deleted, substituted and/or added in the amino acid sequence shown in SEQ ID NO: 1 and which protein has neurite-outgrowth inhibition activity" refers to a gene encoding a so-called "modified protein" of the novel Semaphorin of the present invention which has neurite-outgrowth inhibition activity. Those skilled in the art may easily obtain a gene encoding such protein, for example, by site-directed mutagenesis (*Methods in Enzymology*, 100, 448— (1983)) or PCR method ("Molecular Cloning", 2nd ed., Chapter 15, Cold Spring Harbor Laboratory Press (1989); "PCR A Practical Approach", IRL Press, 200-210 (1991)). In this context, the number of amino acid residues to be deleted, substituted and/or added is to be such a number that permits the deletion, substitution and/or addition by a well-known method such as site-directed mutagenesis described above.

For the purpose of the present invention, a protein "which has neurite-outgrowth inhibition activity" refers to such a protein that has collapse activity on growth cone of neuron or that has neurite-outgrowth inhibition activity. Specifically, these activities may be measured by the following procedures.

The collapse activity on growth cone of neuron may be measured by making reference to M. Igarashi et al., *Science*, vol. 259, pp. 77-79 (1993)), while the neurite-outgrowth inhibition activity may be measured by making reference to, for example, J. A. Davies et al., *Neuron*, vol. 2, pp. 11-20 (1990) or M. Bastmeyer, *J. Neurosci.*, vol. 11, pp. 626-640 (1991)).

Briefly, the former activity is measured by adding an expression product derived from the gene of the present invention to neurons cultured under conventional conditions (e.g., "Culturing, Nerve Cells" edited by Banker et al., MIT Press (1991)) in a culture container coated with a substance promoting the neurite outgrowth and the growth-cone formation such as laminin, collagen, polylysine or polyornithine. After the addition, when a sufficient time has passed to induce collapse of growth cone (typically from 30 minutes to one hour after the addition), those neurons are fixed with 1% glutaraldehyde or the like, and the number of the growth cones which have been collapsed is counted under a microscope. Normalization of the samples is typically carried out on the basis of the total amounts of protein included within the samples.

On the other hand, to measure the latter activity, for example, a mass of cells expressing a gene of the present invention described above is co-cultured with neurons in a collagen matrix, and inability of the neurons to outgrow towards said mass of cells expressing the gene or inhibition of the neurite outgrowth is used as an indicator.

Alternatively, a nervous tissue may be trypsinized, and the single cells thus obtained are treated with culture supernatant from cells expressing a gene of the present invention. Significant decrease in the number of neurons having outgrown neurites relative to the control may be used as an indicator.

Examples of modified proteins obtained above are the human and mouse types of modified protein of Semaphorin of the present invention.

3) Gene Hybridizing Under Stringent Conditions to the Novel Semaphorin Gene

Of the above-mentioned genes, "a gene comprising DNA which hybridizes under stringent conditions to DNA comprising the base sequence shown in SEQ ID NO: 2 and which encodes a protein having neurite-outgrowth inhibition activity" may refer to any mammal type of the novel Semaphorin such as the human or rat type of Semaphorin of the present invention. In addition, any genes which hybridize under stringent conditions to DNA comprising the base sequence shown in SEQ ID NO: 2 are included in the genes of the present invention, provided that they have neurite-outgrowth inhibition activity. Based on the results of a search through EST database, the human type of novel Semaphorin of the present invention obtained by cloning techniques is believed to comprise, as a partial sequence, the sequence from position 1 to position 200 of Accession Number W16752 or to comprise a sequence extremely analogous (more than 95%, and preferably more than 98% identical) to said sequence. Accordingly, the human type of novel Semaphorin gene of the present invention can be easily cloned on the basis of the EST sequence described above. Libraries used for such screening may be human genomic libraries or human cDNA libraries, and cDNA libraries derived from tissues of human nervous system are preferably used.

As used herein, a gene "which hybridizes under stringent conditions" refers to such a gene that hybridizes under conditions described below in Example 1 wherein the salt concentration is 5×SSPE and the temperature is around 42° C.

Also included within the scope of DNA of the present invention are those DNAs cloned from a human cDNA library or a human genomic library which hybridize under stringent conditions to DNA comprising at least part of DNA consisting of the base sequence shown in SEQ ID NO: 2.

Method for cloning such genes may be found, for example, in "Molecular Cloning", 2nd ed., Cold Spring Harbor Laboratory Press (1989), or "PCR" edited by McPherson et al., IRL Press (1991). A preferred library used herein is a human genomic library. DNAs of the present invention may also be cloned based on the sequence from position 1 to position 200 of Accession Number W16572 of the EST database, as described above.

The DNAs cloned as above include full-length DNAs, DNA fragments consisting of about 100 bases or more, and a single-stranded forms (coding strands or complementary stands thereof) of said DNA fragments. In some preferred embodiments, they may be genomic DNA such as 5' transcriptional control region, 3' transcriptional control region, noncoding sequence of exons, introns or the like. Such sequences which don't encode any amino acids are also quite useful, for example, in developing a medicine using antisense nucleotides described below.

In the present invention, "proteins" refers to those proteins which may be obtained by expressing the genes (DNAs) of the present invention. A specific example is a novel mouse Semaphorin having the amino acid sequence shown in SEQ ID NO: 1 which is encoded by the longest open reading frame having the base sequence from position 370 to position 2694 of SEQ ID NO: 2. This Semaphorin has a semaphorin domain which corresponds to the amino acid sequence from position 49 to position 572 of SEQ ID NO: 1. The above novel mouse Semaphorin also contains a signal sequence at its N-terminus, and said signal sequence may undergo processing to be removed during its transfer to membrane, resulting in a mature protein. In the case of SEQ ID NO: 1, the mature form is presumed to be a protein consisting of the amino acid sequence beginning at position 20. Since such mature form or modified protein thereof may also be obtained by expressing a gene of the present invention described above, it is also included within the proteins of the present invention.

Expression vectors used in the present invention are not specifically restricted so far as they are expressible vectors into which a gene or DNA of the present invention is inserted, and specific examples are known expression vectors such as pET, pCDM8 and the like.

A transformant of the present invention is obtained by introducing an expression vector described above into desired host cells. Host cells may be prokaryotic or eukaryotic, and are selected depending on the expression vector used. Those transformants in which the foreign gene existing in the expression vector is stably retained in the cells are more preferred.

The expression vector may be suitably introduced into cells by any one of known methods such as the calcium phosphate method, DEAE-dextran method, or electroporation ("Current Protocols in Molecular Biology", F. M. Ausubel et al. ed., John Wiley & Sons (1987)).

A recombinant protein of the present invention is a protein which is obtained by culturing the above transformants and recovering the recombinant protein expressed and which has neurite-outgrowth inhibition activity. Since Semaphorin of the present invention is presumed from its structure to be a secretory protein, the culture supernatant from transformed cells may probably contain the Semaphorin. Therefore, activity measurement of said Semaphorin can be easily carried out as described above by using the culture supernatant as such.

In addition, the recombinant protein produced may be easily purified by a method such as conventional column chromatography or affinity purification using an antibody of the present invention described below.

"Peptide", as used herein, refers to a peptide fragment comprising a segment of at least six amino acids in the amino acid sequence of a protein of the present invention. In this context, the limitation "at least six amino acids" is based on the fact that a minimal size of peptide capable of forming a stable structure consists of six amino acids, and preferred peptides are those consisting of eight or more amino acids, more preferably of about 10-20 amino acids. A short peptide such as those consisting of about 10-20 amino acids can be synthesized on a peptide synthesizer, while a longer peptide can be obtained by preparing DNA through conventional genetic engineering (for example, using treatments with restriction enzymes), and expressing it in, for example, animal cells. The peptide thus prepared may also be modified by conventional methods.

These peptides can be used as pharmaceutical agents as described below, and can also be used for producing antibodies.

"Antisense nucleotide" which is directed against a segment of at least eight or more bases in a gene or DNA of the present invention refers to a so-called antisense oligonucleotide, antisense RNA, or antisense DNA, and it may be artificially prepared using a synthesizer, or may be obtained by, for example, expressing a gene in the direction opposite to the usual case (i.e., in the antisense direction). Antisense nucleotides are used for inhibiting expression of Semaphorin of the present invention, and can also be used as laboratory reagents for, for instance, in situ hybridization.

A "chemically modified variant" of the above antisense nucleotide refers to such a chemically modified variant that can enhance the transferability of the antisense nucleotide into cells or the stability of the antisense nucleotide in the cells. Examples of such chemically modified variant are phosphorothioate, phosphorodithioate, alkyl phosphotriester, alkyl phosphonate, alkyl phosphoamidate and the like derivatives, and such variants may be prepared in accordance with known references ("Antisense RNA and DNA", WILEY-LISS, 1992, pp. 1-50; J. Med. Chem., 36, 1923-1937 (1993)).

When introduced into cells, the above antisense nucleotides or chemically modified variants thereof can inhibit expression of a protein of the present invention. mRNAs produced by usual gene transcription are sense-strands, and the antisense nucleotides or chemically modified variants thereof can bind to such a sense-strand mRNA in cells to inhibit translation of the particular mRNA, resulting in inhibition of production of Semaphorin of the present invention. Because of such an effect of the antisense nucleotides or chemically modified variants thereof, they may serve as CNS-neuron regeneration promoters as described below.

It can easily be determined whether a particular antisense nucleotide prepared, or a chemically modified variant thereof, has a desired inhibitory effect or not, for example, by one of the following two methods. In one method, an antisense oligonucleotide or chemically modified variant thereof itself is directly introduced into cells expressing a novel Semaphorin of the present invention, and change in expression of said Semaphorin is then used as an indicator. In the other method, a gene capable of producing, when transcribed, said antisense RNA is introduced into the above Semaphorin-expressing cells, and change in expression of said Semaphorin is then used as an indicator.

Preferred examples of antisense nucleotides having such an expression-inhibiting effect are those oligonucleotides having sequences complementary to the transcription initiation site, translation initiation site, 5' noncoding region, exon-intron junction region, or 5' CAP region.

Antibodies of the present invention may be either polyclonal or monoclonal antibodies which specifically bind to a protein or peptide of the present invention. Such antibodies can easily be produced by immunizing an animal such as mouse or rabbit using a protein or peptide of the present invention in whole or in part according to the procedures described in, for example, "Current Protocols in Immunology", pp. 2.4.1-2.6.6 (J. E. Coligan ed., 1992). Fragments of antibodies obtained by purifying the above antibodies and degrading them with a peptidase are also included within the antibodies of the present invention. Such antibodies may be used, for example, in affinity chromatography or screening of cDNA libraries, and as pharmaceutical or diagnostic agents, or laboratory reagents.

The screening method for antagonists of a novel Semaphorin of the present invention refers to, for example, such a screening method of searching for substances which inhibits the neurite-outgrowth inhibition activity of a novel Semaphorin of the present invention. Such screening can be easily carried out by adding the above Semaphorin of the present invention to an assay system for Semaphorin activity described above, and further adding thereto a test substance (for example, a peptide, modified protein, low molecular weight compound or the like). In particular, inhibition of an activity (for example, the neurite-outgrowth inhibition activity) of Semaphorin of the present invention resulted from the addition of the test substance to the culture medium throughout the incubation period or only temporarily in the incubation period can be used as an indicator in the activity assay carried out with an added protein such as Semaphorin of the present invention. It is also important to confirm that the test substance alone does not influence the survival, neurite outgrowth and the like of neurons at the same concentration. When both of these requirements are fulfilled, one can consider the test substance as an antagonist of Semaphorin of the present invention. Although it is preferred to prepare in advance the test substance in the form of aqueous solution, an organic solvent such as DMSO may also be used as a solvent. In any cases, it is important to minimize the volume of solvent so as to exclude any effects of the solvent on neurons. Specifically, the volume to be added should be less than an equal volume, preferably less than $1/10$ volume, and more preferably less than $1/100$ volume relative to the culture medium. Some of antagonists of a novel Semaphorin of the present invention thus obtained will serve as CNS-neuron regeneration promoters as described below.

A transgenic animal of the present invention is produced by artificially inserting a gene or DNA of the present invention into the chromosome, or by knocking out said gene or DNA. Accordingly, the transgenic animals of the present invention include not only animals which expresses DNA of the present invention, but also so-called knockout animals in which DNA of the present invention is destroyed and dysfunctional. Destruction of DNA may be achieved by a known method (Shinichi Aizawa, "Gene Targeting", Yodosha, 1995).

Animals used herein may be those aminmals other than human, for example, laboratory animals such as mouse, rat, hamster, and rabbit, or domestic animals such as bovine and swine, and mouse is suitably used because of remarkable development of cell technology for mouse.

Methods for producing a transgenic animal are briefly described below for a transgenic mouse by way of illustration. For example, in the first method, DNA is microinjected into a pronucleus of an fertilized ovum of mouse. In the second method, DNA is introduced by infecting an eight cell stage embryo with a recombinant retrovirus. In the third method, DNA is introduced into an embryonic stem cell (ES cell) having totipotency, for example, by electroporation, and the cell is injected into another blastula to produce a chimera. See, "Manipulation of Mouse Embryo", B. Hogan et al. ed., 1986, Cold Spring Harbor Laboratory, and Shinichi Aizawa, "Gene Targeting", 1995, Yodosha.

Transgenic animals produced by the above methods are quite useful as an animal model for developing pharmaceutical agents or an animal used for a screening of pharmaceutical agents.

The usefulness of the novel Semaphorin and others of the present invention (proteins, DNAs, or peptides of the novel Semaphorin, antisense nucleotides or antibodies against the Semaphorin, and transgenic animals) is described below.

1) Usefulness as Reagents in Relevant Area of Investigation

While Semaphorin of the present invention inhibits neurite-outgrowth as described above, it has been also suggested that Semaphorin gene may have other unknown functions such as immunosuppression (*Cell*, 75, 1389-1399 (1993)). Accordingly, it is quite important for studies in relevant field to investigate expression of Semaphorin gene or distribution and function of Semaphorin protein. The present invention can provide DNAs, proteins, peptides, antibodies, antisense nucleotide, transgenic animals and the like which can be used for such purposes. Since the novel Semaphorin of the present invention is a secretory protein, it may be advantageously used as laboratory reagents.

2) Usefulness as Pharmaceutical or Diagnostic Agents

One embodiment of the protein of the present invention is a protein which inhibits neurite outgrowth. Accordingly, such a protein may serve as therapeutic agent for immune diseases such as atopic dermatitis, pain or other diseases by virtue of their inhibition activity on neurite outgrowth of PNS-neurons.

In addition, as described in the "Background Art" section, it has been recently suggested that a certain Semaphorin may play an important role also in peripheral non-nervous systems. In particular, it has been suggested that a certain Semaphorin may act in inhibiting the growth of cardiac muscles (*Nature*, 383, 525-528 (1996)). Also in the immune system, a certain Semaphorin has been suggested to be involved in survival and aggregation of B lymphocytes (*Proc. Natl. Acad. Sci. USA*, 93, 11780-11785 (1996)). It has also been suggested more recently that a certain Semaphorin may play some role in the immune reactions in rheumatism (*B.B.R.C.*, 234, 153-156 (1997)). Involvement of Semaphorin in lung cancer has also been suggested (*Proc. Natl. Acad. Sci. USA*, 93, 4120-4125 (1996)).

Furthermore, it is believed because of the following reasons that Semaphorin of the present invention can inhibit cell movement such as cell migration or infiltration. While actin cytoskeleton plays an important role in movement of cell itself, it has been demonstrated that actin cytoskeleton similarly plays an important role also in movement of growth cone of neurons. It has been also demonstrated that formation of actin cytoskeleton in both cases is regulated by similar mechanisms in which G protein belonging to the Rho family is involved (*Genes Develop.* 8, 1787-1802 (1994); *Cell*, 81, 53-62 (1995)). Semaphorin of the present invention is presumed to inhibit elongation of growth cone via depolymerization of actin, and it is also conceivable that the same can inhibit movement (such as migration or infiltration) of cells expressing receptors for Semaphorin through similar mechanism. This argument is also supported by an observation that Ephrin known as a neuron guidance factor causing collapse of growth cone as Semaphorin did inhibit migration of neural crest cells (*Neuron*, 18383-396 (1997)).

In view of the above findings taken together, it is expected that the novel Semaphorin proteins, DNAs and the like of the present invention may inhibit infiltration or migration of cancer cells or immunocytes, and therefore, may be used as antiallergic agents, immunosuppressive agents, or anti-tumor agents.

In addition, as described below in Example 2, the novel Semaphorin of the present invention is expressed in a wide range of peripheral tissues and in a localized manner, suggesting that it may play some role at these sites or in the neighborhood thereof. In that case, the novel Semaphorin of the present invention may serve as therapeutic or diagnostic agent for diseases at the sites of expression indicated in Example 2.

As described in the above section 1), since the novel Semaphorin of the present invention is a secretory protein, it may be advantageously used as pharmaceutical or diagnostic agents.

On the other hand, it is suggested that a substance which inhibits the binding of natural Semaphorin to Semaphorin receptors may act as an antagonist inhibiting the neurite-outgrowth inhibition effect of Semaphorin. Since Semaphorin of the present invention is expressed also in the central nervous system, it is also presumed to be a CNS-neuron regeneration inhibitor. In that case, peptides, antibodies, or antisense nucleotides having an ability as an antagonist may promote regeneration of CNS-neurons, and therefore, may serve as therapeutic agents for spinal cord injury etc. Such antagonists include those substances found by the screening method described above.

The novel Semaphorin and other substances of the present invention, of which usefulness as pharmaceutical or diagnostic agents was described above, may be administered in doses and by administration methods as described below. For example, Semaphorin proteins, peptides, or antibodies may be formulated with an appropriate stabilizing agent, buffer and/or diluent, and used in an amount of several hundreds µg to 2 g, and preferably of several tens mg or less, per administration. To reduce the administration frequency, it is possible to use a sustained release preparation, or to administer a formulation by portions over a prolonged period by means of, for example, an osmotic pump. Alternatively, cells expressing said Semaphorin protein or other substances may also be implanted into a living body for that purpose.

In the case in which an antisense nucleotide is used as pharmaceutical agents, such an antisense oligonucleotide or chemical variant thereof may be administered as such or an antisense RNA may be produced in cells, with doses and administration methods as described below.

In the method in which an antisense oligonucleotide or, chemically modified variant thereof is administered as such, the antisense oligonucleotide preferably has a length of, for example, 5-200 bases, more preferably 8-25 bases, and especially preferably 12-25 bases. Antisense oligonucleotide or chemically modified variant thereof may be formulated by mixing it with a stabilizing agent, buffer, solvent and the like prior to its administration. Such formulation may optionally be co-administered with, for example, an antibiotic, antiinflammatory, or anesthetic agent. Although the formulation thus prepared may be administered via various routes, it is preferred to topically administer at the site disordered. To avoid frequent administrations, a sustained release mini-pellet preparation may be prepared and embedded near the affected site. Alternatively, a formulation may be gradually and continuously administered to the affected site by means of, for example, an osmotic pump. The dose is typically adjusted so that the concentration at the site of action will be 0.1 nM to 10 μM.

In the method in which an antisense RNA is produced in cells, the antisense RNA preferably has a length of, for example, more than 100 bases, preferably more than 300 bases, and more preferably 500 bases or more.

The methods by which a gene expressing an antisense RNA is introduced into a patient include an in vivo method in which the gene is directly introduced into cells in a living body, and an ex vivo method in which the gene is introduced into particular cells ex vivo and the cells are returned into the body (*Nikkei Science*, April, 1994, pp. 20-45; *Gekkan-Yakuji*, 36 (1), 23-48 (1994); *Jikkenn-Igaku-Zokan*, 12 (15), 1994; and references cited therein). An in vivo method is more preferred.

Such in vivo methods include a method employing recombinant viruses and other methods (*Nikkei Science*, April, 1994, pp. 20-45; *Gekkan-Yakuji*, 36 (1), 23-48 (1994); *Jikken-gaku-Zokan*, 12 (15), in its entirety (1994); and references cited therein).

The methods employing recombinant viruses may include a method in which Semaphorin gene is incorporated into a virus genome of, for example, retrovirus, adenovirus, adeno-associated virus, herpesvirus, vaccinia virus, poliovirus, or sindbis virus, and the recombinant virus is introduced into a living body. Among these methods, those employing retrovirus, adenovirus or adeno-associated virus are particularly preferred.

Other methods may include a liposome method or a lipofectin method. The liposome method is particularly preferred.

For the ex vivo methods, microinjection, the calcium phosphate method, electroporation and the like may also be used, besides those techniques described above.

Administration of the gene to a patient is carried out via appropriate routes depending on, for example, the particular disease or symptom to be treated. For example, it may be administered intravenously, intraarterially, subcutaneously, or intramuscularly, or directly administered into the affected site such as nerve. For example, when spinal cord is infected with the recombinant virus, the expression of Semaphorin gene is inhibited exclusively in the spinal cord. Expression of an antisense nucleotide of the present invention typically lasts several days to several months, and such single infection is sufficient to allow regeneration of neuron. Re-infection may also be possible, when the antisense nucleotide is weakly expressed. When administered by an in vivo method, the gene may be formulated in the form of, for example, a solution, and typically it is formulated in the form of an injection containing an antisense nucleotide as an active ingredient to which conventional carrier or other additives may be added as needed. In the case of liposomes or membrane-fused liposomes (such as Sendai virus (HVJ)-liposomes) containing an antisense nucleotide, the liposome preparations may be in the form of a suspension, a frozen preparation, a centrifugally-concentrated frozen preparation or the like.

Although the amount of antisense nucleotide in the formulation may vary depending on, for example, the disease to be treated, the age and weight of the patient, it is typically 0.0001-100 mg, and preferably 0.001-10 mg. Such formulation is preferably administered once every several days to several months.

EXAMPLES

Figure 1:
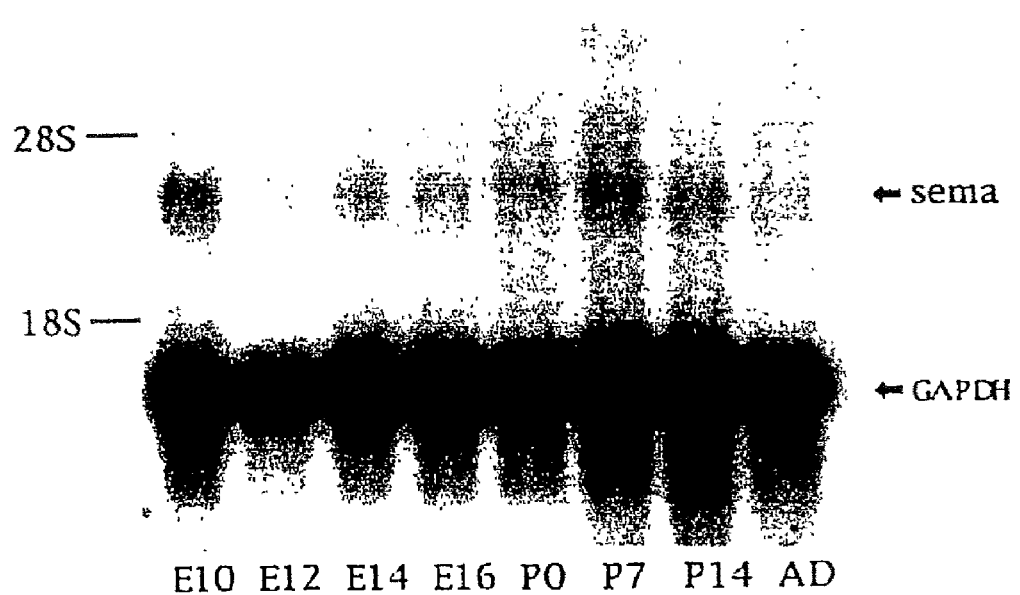
FIG. 1 shows a picture of electrophoresis obtained using Northern blotting technique described in Example 3. In this figure, lanes E10, E12, E14, E16, P0, P7, P14 and AD indicate the results for embryonic day-10, embryonic day-12, embryonic day-14, embryonic day-16, postnatal day-0, postnatal day-7, postnatal day-14 and the adult, respectively. The upper arrow indicates the band for the novel Semaphorin of the present invention, and the lower arrow indicates the band for GAPDH [2].

The present invention is further illustrated by the following Examples. The present invention is not, however, limited by such Examples in any way.

Example 1

Cloning of a Novel Semaphorin Gene

1) Amplification of cDNA Fragment Encoding Semaphorin Domain

From an embryonic day-14 embryo of ICR mouse (Kiwa Jikken Dobutsu), mRNA was isolated using FastTrack (Invitrogen), and single-stranded cDNA was synthesized using said mRNA as a template together with MLV reverse transcriptase and random hexamer primer. In order to amplify the region homologous between known Semaphorin genes Collapsin and G-Sema I (*Cell*, 75, 217-227 (1993)), PCR was carried out under the conditions described in *FEBS. Lett.*, 370, 269-272 (1995) using the above single-stranded cDNA as a template together with the following two synthetic oligonucleotide primers:

```
                                         (SEQ ID NO: 3)
5'-T A C G A C G T N (A/C/T) T N T T (C/T) A T
(A/C/T) G G-3'
and
                                         (SEQ ID NO: 4)
5'- T C C C A I G C (A/G) C A (A/G) T A I G G
(A/G) T C-3'.
```

The resulting PCR product was subjected to 1.5% agarose gel electrophoresis to separate and purify a DNA fragment having an expected size of about 300 bp. This DNA fragment was inserted into pCRscript SK(+) (Stratagene), and used as a probe in the following cDNA library screening.

2) Isolation of cDNA Clone

The cDNA fragment of about 300 bp obtained in the above section 1) was labeled with $^{32}$P using Random Priming (Pharmacia), and used as a probe in screening of an adult mouse brain cDNA library (Stratagene) as follows. The phage DNAs constituting said cDNA library were transferred onto nylon filters (Hybond-N; Amersham), denatured, neutralized, and then Fixed on the filters. These filters were then hybridized with the above probe to obtain positive clones. The hybridization was carried out in a hybridization buffer (5×SSPE (0.9M NaCl, 50 mM NaH$_2$PO$_4$<pH 7.7), 5 mM EDTA, 45% formaldehyde, 5×Denhardt's solution, 0.5% SDS, 20 µg/ml denatured salmon sperm DNA) for 16 hours at 42° C.

3) DNA Sequencing

Of the clones obtained in the above section 2), the base sequence of a clone containing the longest cDNA was determined by the dideoxy chain termination method using Taq Dye Primer cycle sequencing kit or Taq Dye Terminator cycle sequencing kit and ABI 373 A DNA sequencer (Applied Biosystems). The base sequence of cDNA thus determined is shown in SEQ ID NO: 2. The longest open reading frame corresponds to the region from position 370 to position 2694 of SEQ ID NO: 2, and the amino acid sequence corresponding to said ORF is shown in SEQ ID NO: 1.

Comparison of the base sequence shown in SEQ ID NO: 2 with known base sequences from databases revealed that the gene is a novel one. In addition, the region from position 49 to position 572 of the amino acid sequence shown in SEQ ID NO: 1 has homology with a so-called semaphorin domain sequence, and the amino acid sequence contains thirteen cysteines well conserved among Semaphorin genes, definitely confirming that it is a novel Semaphorin belonging to the Semaphorin family.

Since the novel Semaphorin of the present invention has an immunoglobulin-like domain at positions 591 to 659 of its amino acid sequence but has no transmembrane regions, it presumably belongs to the secretory Semaphorin subfamily.

*E. coli* strain JM109 (pSRαmS(I)), a transformant obtained by introducing a plasmid pSRαmS(I), which incorporates the full-length cDNA for the novel Semaphorin gene of the present invention in pUCSRα, into *E. coli* strain JM109, has been deposited at the National Institute of Bioscience and Human Technology (1-1-3 Higashi, Tsukuba, Ibaraki, Japan) under Deposit No. FERM BP-6157 on Oct. 24, 1997.

Example 2

Analysis of Distribution of the Novel Semaphorin Gene Expression by In Situ Hybridization 1) Method 1. Slide Preparation Various organs sampled from ddY mouse (purchased from SLC) were frozen with dry ice powder, and sliced into 14-µm thick sections at −15° C. using a cryostat to obtain prepared slides.

2. Preparation of Probe

A BamH I-EcoR I fragment (about 680 bp) of the cDNA obtained in Example 1-3) was inserted into Bluescript KS+ (Stratagene), and the resultant construct was then cut with BamH I. The DNA thus obtained was used as a template to prepare an antisense RNA probe labeled with $^{35}$S-UTP using T3 RNA polymerase.

3. Pretreatment of Slides

The sections obtained in the above step 1 were fixed with 10% formalin solution for 20 minutes, washed twice with PBS, and treated with 50 mM Tris-HCl (pH 8.0)/5 mM EDTA solution containing 10 µg/ml protease K for 5 minutes. After washing once with PBS, these sections were fixed again with 10% formalin solution for 5 minutes, and treated with 0.1 M triethanolamine solution containing 0.25% acetic anhydride for 10 minutes. Furthermore, these sections were washed once with PBS, and successively treated with 70%, 90% and 100% alcohol for dehydration.

4. Hybridization

The probe prepared in the above step 2 was added to a hybridization buffer (50% formamide, 20 mM Tris-HCl (pH 8.0), 5 mM EDTA, 0.3 M NaCl: 1% Denhardt's solution, 0.2% Sarkosyl, 200 µg/ml yeast tRNA, 200 µg/ml salmon sperm DNA) so that an amount of the buffer to be used for each slide contained 1×10$^6$ cpm probe. The buffer was placed onto the slides, incubated overnight at 55° C., and the slides were then subjected to the following procedures:

(1) incubation for 15 minutes at 55° C. in 5×SSC, 1% 2-mercaptoethanol solution;

(2) incubation for 30 minutes at 65° C. in 2×SSC, 50% formamide, 5% 2-mercaptoethanol solution;

(3) incubation for 30 minutes at 37° C. in 10 mM Tris-HCl, 1 mM EDTA, 0.5 M NaCl solution;

(4) incubation for 30 minutes at 37° C. in the solution described in the above step (3) containing 1 mg/ml RNase A;

(5) incubation for 30 minutes at 65° C. in 2×SSC, 50% formamide, 5% 2-mercaptoethanol solution;

(6) incubation for 10 minutes at room temperature in 2×SSC; and (7) incubation for 10 minutes at room temperature in 0.1× SSC.

At the end, the slides were successively treated with 70%, 90%, and 100% alcohol for dehydartion.

5. Autoradiography

Microautoradiography was carried out using a photographic emulsion (Ilford K-5, Ilford).

2) Results

The novel Semaphorin gene of the present invention is mainly distributed at the following sites (the distribution in mature mouse, unless indicated as "neonatal mouse").

(1) Peripheral Tissues

Tooth (Expression in Neonatal Mouse)
  odontoblast
Inner Ear (Expression in Neonatal Mouse)
  spiral ganglion
  epithelium of semicircular canal
  macula of utricle
  macula of saccule
Lung
  trachea
  epithelium to smooth muscle layer of bronchus and bronchiole
Kidney
  glomerulus or visceral layer of Bowman's capsule
Ovary
  granular layer of ovarian follicle
Skin
  hair matrix
Cartilage of Face, Backbone and the Like
Hair Root of Palp and its Periphery (2) Central Nervous System Eyeball
  lamina ganglionaris and inner granular layer of retina
Hlippocampus
Cerebral Cortex
  lamina profunda (layer 5/6)
  basal ganglia (corpus striatum, globus pallidus, diagonal band nucleus)
  reticular nucleus of thalamus Cerebellum
    granule cell layer
Olfactory Bulb
    glomerular layer
    mitral cell layer
    inner granular layer
Nucleus Pontis
    nucleus of the spinal tract of the trigeminal nerve
    main sensory nucleus of the trigeminus
Neurons in Part of Dorsal Root Ganglion (Expression in Neonatal Mouse)
Tractus Solitarius Nucleus
Reticular Formation Example 3

Analysis of Distribution of the Novel Semaphorin Gene Expression by Northern Analysis 1) Method From pregnant ddY mice, fetal mice at embryonic days-10, 12, 14, and 16 (considering the day on which the presence of vaginal plug was confirmed as embryonic day-0) were sampled. mRNAs from the whole body of embryonic day-10 embryo, the head of embryonic day-12 embryo, or the brain of embryonic day-14 or 16 embryo, postnatal day-0, 7, 14, or mature mouse were purified using QuickPrep Micro mRNA Purification Kit (Pharmacia). Each 4 µg per lane of mRNAs was subjected to electrophoresis on 1% agarose-formaldehyde gel, and then transferred onto a nylon membrane (Hybond-N, Amersham). A probe labeled with [$\alpha$-$^{32}$P]dCTP was prepared using a Xba I-Hind III fragment (about 790 bp) of cDNA obtained in Example 1-3) as a template together with Random Labeling Kit (Pharmacia). In the same manner, GAPDH [2] was also labeled as an internal standard.

The above probe and GAPDH [2] were added to a hybridization solution (50% formamide, 5×SSC, 5×Denhardt's solution, 25 mM sodium phosphate buffer (pH 6.8), 5 mM EDTA, 0.1% SDS, 20 µg/ml salmon sperm DNA) so that the solution contained each 1×10$^6$ cpm/ml of the labeled compounds, and hybridized overnight at 42° C. with the above nylon membrane. The nylon membrane was finally washed three times for 10 minutes and three times for 20 minutes in 0.1×SSC, 0.1% SDS at 65° C., and then exposed overnight on Bio-Imaging Analyzer BAS 1000 (Fuji Film) to detect labeled bands.

2) Results

The results are shown in FIG. 1. Expression of the novel Semaphorin gene of the present invention can be observed at all stages studied.

Example 4

Expression of the Novel Semaphorin in Animal Cells

In order to express the novel Semaphorin of the present invention, the novel Semaphorin gene of the present invention obtained in Example 1-2) was introduced into NIH 3T3 cells.

First of all, the coding region of the novel Semaphorin cDNA obtained in Example 1-2) was inserted into AP (alkaline phosphatase)-1 vector (Flanagan, J. G. and Leader, P., Cell, vol. 63, pp. 185-194 (1990)) to construct a vector for expressing a novel Semaphorin-alkaline phosphatase fusion protein.

Two µg of the above vector DNA was introduced into NIH 3T3 cells by the calcium phosphate co-precipitation method according to the procedures described in Flanagan, J G. and Leder P., *Cell*, vol. 63, pp. 185-194 (1990). After 24 hours, the cells were trypsinized to detach, and suspended in DMEM containing 10% FCS (Gibco BRL). The cell suspension was plated into a 98-well dish, and the incubation was continued to screen for transformed cells which stably express alkaline phosphatase activity in the presence of Geneticin. Measurement of alkaline phosphatase activity was achieved as follows: the culture supernatant from the above-mentioned transformed cells was sampled; p-nitrophenyl phosphate, a substrate of alkaline phosphatase, was added thereto to develop the color; and the absorbance at 405 nm ($OD_{405}$) was then measured (Flanagan, J G. and Leder, P., *Cell*, vol. 63, pp. 185-194 (1990)).

As a result, transformed cells stably expressing alkaline phosphatase activity were obtained, and these cells were subjected to the activity measurement described below in Example 5 as the cells expressing a fusion protein of a novel Semaphorin of the present invention with alkaline phosphatase. In parallel, the same experiment as described above was repeated using AP-1 vector having no inserted Semaphorin cDNA to prepare control transformed cells expressing only alkaline phosphatase.

Example 5

Activity Measurement of the Novel Semaphorin (1)

The cDNA obtained in Example 1-2) is inserted into a plasmid pUCSRα to construct an expression plasmid. This expression plasmid is transfected into COS 7 cells by DEAE-dextran method, and the culture supernatant is recovered after one day and after two days. The culture supernatant thus obtained and a control culture supernatant from untransfected COS 7 cells are each added to culture medium of neurons which have been overnight-cultured in vitro and thus have well-outgrown neurites, and the growth-cone collapse activity is measured by the method described in M. Igarashi et al., *Science*, vol. 259, pp. 77-79 (1993). As a result, it is demonstrated that the culture supernatant from COS 7 cells expressing Semaphorin gene of the present invention has significantly higher growth-cone collapse activity.

Activity Measurement of the Novel Semaphorin (2)

The cDNA obtained in Example 1-2) is inserted into a plasmid pUCSRα to construct an expression plasmid. This expression plasmid is transfected into COS 7 cells by DEAE-dextran method. After allowing the expressing cells to form a cell mass, it is enclosed in a collagen gel matrix containing an appropriate culture medium at an appropriate distance from neurons. In parallel, a mass of untransfected COS 7 cells as a control is also enclosed similarly. By examining the neurite outgrowth after culturing for several days, it is shown that the neurite outgrowth towards COS 7 cells expressing Semaphorin gene of the present invention is inhibited.

The same experiment may also be carried out using the novel Semaphorin-expressing NIH 3T3 transformed cells prepared in Example 4.

In particular, a tissue piece of dorsal root ganglion removed from mouse embryo at embryonic day-12.5 to 14.5 by a convention method is firstly placed into a culture medium (Hanks' solution; Nissui Pharmaceutical Co.). The tissue piece of dorsal root ganglion is positioned at a distance of 400-800 µm from cell masses of the NIH 3T3 cells expressing the novel Semaphorin of the present invention (cells expressing a fusion protein of the novel Semaphorin with alkaline phosphatase) prepared in Example 4, and of control NIH 3T3 cells (cells expressing only alkaline phosphatase) prepared in Example 4, and all the cell masses and tissue piece are enclosed in a collagen gel matrix. The collagen gel matrix is prepared according to the method of Tessier-lavigne, M. and Goodman, C. S., Science, 274, 1123-1133 (1996) by mixing collagen, 10×BME and NaHCO$_3$/NaOH at the ratio of 8:1:1, and incubating the mixture for 30 minutes at 37° C. to polymerize, and 2 ml of a culture medium (DMEM containing 10% FCS (Gibco BRL)) supplemented with 50 ng/ml mouse NGF (Boehringer Mannheim) is added to the collagen gel matrix.

After culturing 24-46 hours, the above dorsal root ganglion and NIH 3T3 cells are fixed with a phosphate buffer containing 4% paraformaldehyde, and observed under Olympus IMT-2 inverted phase-contrast microscope. Neurite outgrowth is determined by measuring the distance from the outer edge of dorsal root ganglion tissue piece to the rim of outspread neurites (Messersmith et al., Neuron, 14, pp. 949-959 (1995)).

Figure 2:
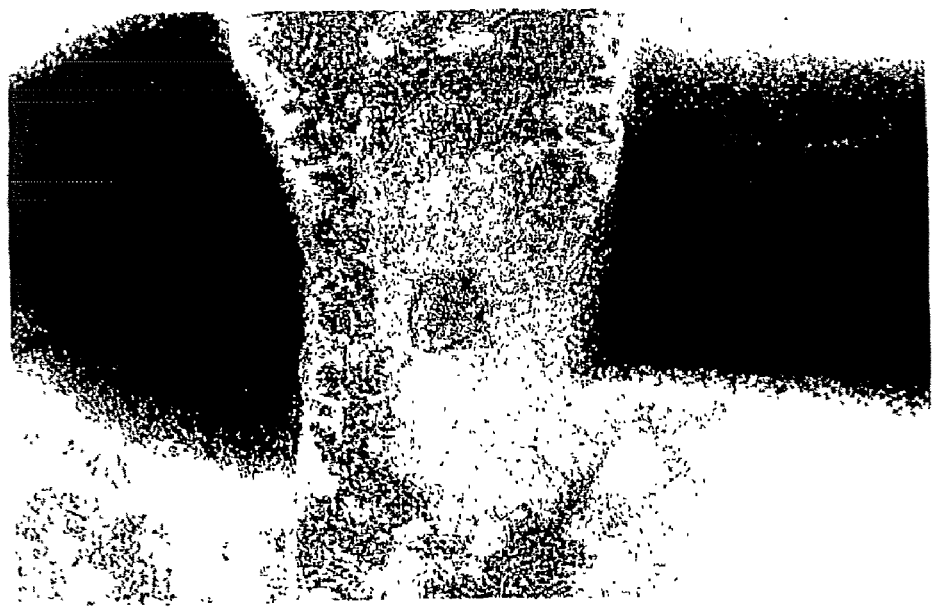
FIG. 2 shows a photomicrograph indicating the result of the activity measurement of the novel Semaphorin (2) described in Example 5. A tissue piece of dorsal root ganglion can be seen at the center of this figure. The dark area at the left side indicates a cell mass of NIH 3T3 cells expressing a fusion protein of the novel Semaphorin with alkaline phosphatase, and the dark area at the right side indicates a cell mass of control NIH 3T3 cells expressing alkaline phosphatase. As can be seen from this figure, the neurite outgrowth towards the Semaphorin-expressing cells was inhibited compared with that towards the control cells.

As a result, it is shown that the neurite outgrowth towards the side on which the novel Semaphorin-expressing NIH 3T3 cells are placed is significantly decreased compared to that towards the side on which the control NIH 3T3 cells are placed, demonstrating that the novel Semaphorin of the present invention inhibits neurite outgrowth (FIG. 2).

Activity Measurement of the Novel Semaphorin (3)

A tissue piece of dorsal root ganglion at embryonic day-11.5 to 12.5 is dissociated using trypsin. The dorsal root ganglion cells thus isolated using trypsin are inoculated at a low density into a conditioned medium from control culture (culture medium obtained by culturing NIH 3T3 cells transformed with AP-1 vector for four days, and supplemented with 50 ng/ml mouse NGF (Boehringer Mannheim)), or into a conditioned medium obtained by culturing NIH 3T3 cells expressing a fusion protein of the novel Semaphorin of the present invention with alkaline phosphatase for four days to which 50 ng/ml mouse NGF has been added. After culturing at 37° C. for 18 hours, the cells are fixed for one hour with 4% paraformaldehyde. The neurites which have outgrown to the length at least 2-times longer than the diameter of the cell is defined as "neurite", and the number of cells having neurites is counted.

As a result, it is shown that only 12.9% of the dorsal root ganglion cells treated with the culture medium containing the novel Semaphorin of the present invention have neurites whereas 71.9% of the dorsal root ganglion cells treated with the control culture medium have neurites, demonstrating that the novel Semaphorin of the present invention inhibits neurite outgrowth.

Effect of the Invention

The present invention provides a novel Semaphorin having neurite outgrowth inhibition activity and proteins analogous thereto, or peptide fragments of, or antibodies against, such proteins, genes encoding such proteins, expression vectors for said genes, transformed cells into which said expression vectors have been introduced, methods for producing a recombinant protein which employ said transformed cells, antisense nucleotides against the above genes, transgenic animals involving insertion or deletion of the above genes, or screening methods for antagonists of the above proteins. Furthermore, pharmaceutical or diagnostic agents or laboratory reagents employing the above proteins, genes or the like is expected to promote a dramatic advance mainly in diagnoses, treatments, or studies relating to neurological diseases.

The invention claimed is:

1. An isolated polypeptide comprising:
the amino acid sequence shown in SEQ ID NO: 1.

2. An isolated polypeptide obtained by expressing in a cell a nucleic acid comprising a polynucleotide comprising a nucleotide sequence selected from the group consisting of:
(a) the nucleotide sequence of SEQ ID NO:2;
(b) the nucleotide sequence of SEQ ID NO:2 from nucleotide 370 to nucleotide 2694; and
(c) a nucleotide sequence encoding the amino acid sequence of SEQ ID NO:1.

3. An isolated polypeptide obtained by expressing in a cell a nucleic acid comprising a polynucleotide that specifically hybridizes with the full length of the complement of a polynucleotide comprising a nucleotide sequence selected from the group consisting of:
(a) the nucleotide sequence of SEQ ID NO:2; and
(b) the nucleotide sequence of SEQ ID NO:2 from nucleotide 370 to nucleotide 2694; under hybridization conditions of a buffer comprising 45% (v/v) formamide, 5×SSPE at 42° C.,
and washing after hybridization with a buffer comprising 0.1×SSC, 0.1% SDS at 65° C.,
wherein said polypeptide has the biological activity of inhibiting neurite outgrowth from dorsal root ganglion cells.

4. An isolated polypeptide obtained by expressing in a cell a nucleic acid comprising a polynucleotide that specifically hybridizes with the full length of the complement of a polynucleotide having a nucleotide sequence selected from the group consisting of:
(a) the nucleotide sequence of SEQ ID NO:2; and
(b) the nucleotide sequence of SEQ ID NO:2 from nucleotide 370 to nucleotide 2694; under hybridization conditions of a buffer comprising 45% (v/v) formamide, 5×SSPE at 42° C.,
and washing after hybridization with a buffer comprising 0.1×SSC, 0.1% SDS at 65° C.,
wherein said polypeptide has the biological activity of collapsing growth cones of neuronal cells.

* * * * *

UNITED STATES PATENT AND TRADEMARK OFFICE
CERTIFICATE OF CORRECTION

| | | |
|---|---|---|
| PATENT NO. | : 7,932,352 B2 | Page 1 of 1 |
| APPLICATION NO. | : 12/325089 | |
| DATED | : April 26, 2011 | |
| INVENTOR(S) | : Shinobu Inagaki et al. | |

It is certified that error appears in the above-identified patent and that said Letters Patent is hereby corrected as shown below:

The title page item (62) should read:

\*\*(62) Division of application No. 10/144,031, filed on May 14, 2002, now abandoned, which is a division of application No. 09/308,179, filed as application No. PCT/JP97/0411 on Nov. 12, 1997, now Pat. No. 6,436,669.\*\*

The paragraph beginning at column 1, line 1 should read:

\*\*This application is a Divisional of application Ser. No. 10/144,031 filed on May 14, 2002, now abandoned, and for which priority is claimed under 35 U.S.C. § 120; and which is a Divisional of U.S. Application No. 09/308,179 filed on May 14, 1999; now U. S. Pat. No. 6,436,669, which is the International Phase Application of International Application No. PCT/JP97/04111 filed on Nov. 12, 1997; and this application claims priority of Application No. 8/321068 filed in Japan on Nov. 15, 1996 under 35 U.S.C. § 119; the entire contents of all are hereby incorporated by reference.\*\*

Signed and Sealed this

Twentieth Day of September, 2011

David J. Kappos
*Director of the United States Patent and Trademark Office*